(12) United States Patent
Hsieh et al.

(10) Patent No.: US 8,877,496 B2
(45) Date of Patent: Nov. 4, 2014

(54) METHOD FOR TRANSFERRING CELLS TO CARRIERS AND APPLICATION THEREOF

(75) Inventors: Chin-Hsiung Hsieh, Taipei (TW); Yi-You Huang, Taipei (TW)

(73) Assignee: National Taiwan University, Taipei (TW)

(*) Notice: Subject to any disclaimer, the term of this patent is extended or adjusted under 35 U.S.C. 154(b) by 1180 days.

(21) Appl. No.: 12/479,754

(22) Filed: Jun. 5, 2009

(65) Prior Publication Data

US 2010/0136685 A1 Jun. 3, 2010

(30) Foreign Application Priority Data

Dec. 2, 2008 (TW) ................... 97146719 A

(51) Int. Cl.
 C12N 5/00 (2006.01)
 C12N 5/02 (2006.01)
 C12N 11/10 (2006.01)
 C12N 11/08 (2006.01)

(52) U.S. Cl.
 CPC .......... *C12N 5/0068* (2013.01); *C12N 2531/00* (2013.01); *C12N 2533/30* (2013.01); *C12N 2533/54* (2013.01); *C12N 2533/70* (2013.01); *C12N 2533/72* (2013.01)
 USPC ........... 435/373; 435/396; 435/402; 435/178; 435/180; 435/366

(58) Field of Classification Search
 None
 See application file for complete search history.

(56) References Cited

U.S. PATENT DOCUMENTS

| | | | |
|---|---|---|---|
| 4,829,002 A * | 5/1989 | Pattillo et al. ............... 435/297.1 |
| 5,736,398 A * | 4/1998 | Giambernardi et al. ...... 435/383 |
| 5,935,847 A * | 8/1999 | Smith et al. ................. 435/297.5 |
| 5,998,185 A * | 12/1999 | Fuller et al. .................... 435/180 |
| 6,127,168 A * | 10/2000 | Ko ............................. 435/299.1 |
| 6,306,646 B1 * | 10/2001 | Saad et al. ................. 435/305.1 |
| 6,458,565 B1 * | 10/2002 | Cunningham et al. ........ 435/70.3 |
| 7,323,333 B2 * | 1/2008 | Caviedes et al. ............. 435/368 |
| 7,358,082 B2 * | 4/2008 | Tsuzuki et al. ............. 435/293.1 |
| 7,655,457 B2 * | 2/2010 | Kuwabara et al. ......... 435/299.2 |
| 7,745,209 B2 * | 6/2010 | Martin et al. .............. 435/294.1 |
| 7,887,843 B2 * | 2/2011 | Libera et al. .................. 424/489 |
| 2008/0009064 A1* | 1/2008 | Ronfard et al. ............... 435/402 |

FOREIGN PATENT DOCUMENTS

TW 419367 1/2001
TW 233449 6/2005

* cited by examiner

*Primary Examiner* — Taeyoon Kim
*Assistant Examiner* — Srikanth Patury

(57) ABSTRACT

The invention provides a method for transferring cells to carriers, including: (a) providing a hydrophobic cell culture container or a cell culture container coated with a hydrophobic material on a bottom thereof; (b) adding carriers which are more hydrophilic than the hydrophobic cell culture container or hydrophobic materials and a culture medium containing cells into the hydrophobic cell culture container or the cell culture container coated with the hydrophobic material on the bottom thereof; and (c) culturing the cells, wherein the cells attach to the carriers and grow.

13 Claims, 14 Drawing Sheets

METHOD FOR TRANSFERRING CELLS TO CARRIERS AND APPLICATION THEREOF

CROSS REFERENCE TO RELATED APPLICATIONS

This application claims priority of Taiwan Patent Application No. 097146719, filed on Dec. 2, 2008, the entirety of which is incorporated by reference herein.

BACKGROUND OF THE INVENTION

1. Field of the Invention

The present invention relates to a method for culturing cells, and in particular relates to a method for transferring cells to carriers.

2. Description of the Related Art

The three principal parts of tissue engineering comprise cells, signals and scaffolds. The basic process for tissue engineering comprises culturing cells in vitro to reach a sufficient cell mount, filling the cells into the scaffolds, and culturing the cells in the scaffolds. Optionally, a chemical substance or growth factor is needed for promoting cell differentiation. However, in order to increase the efficiency for cells to attach to scaffolds, the scaffold needs to be chemically modified, or during cell culturing other devices or processes are needed.

Taiwan Patent Publication No. 00419367 discloses a method to increase the efficiency for cells to attach to scaffolds, wherein the surface of a substrate is applied with a surface modifier composed of CBD-RGD.

Taiwan Patent No. I233449 discloses another method to increase the efficiency for cells to attach to scaffolds, wherein cells are attached to porous hydrophilic scaffolds filled in the culture tanks, by vertically oscillating medium levels disposed between culture tanks.

However, chemically modifying scaffolds is complicated, and a simple and effective method for transferring cells to carriers is needed.

BRIEF SUMMARY OF THE INVENTION

The invention provides a method for transferring cells to carriers, comprising: (a) providing a hydrophobic cell culture container or a cell culture container coated with a hydrophobic material on a bottom thereof; (b) adding carriers which are more hydrophilic than the hydrophobic cell culture container or hydrophobic materials and a culture medium containing cells into the hydrophobic cell culture container or the cell culture container coated with the hydrophobic material on the bottom thereof; and (c) culturing the cells, wherein the cells attach to the carriers and grow.

The invention also provides a method for culturing cells by stacking cells layer by layer, comprising: (a) culturing a plurality of different types of cells by the method claimed in claim 1, respectively, wherein the plurality of different types of cells attach to the respective carriers; (b) providing another hydrophobic cell culture container or another cell culture container coated with a hydrophobic material on a bottom thereof; (c) adding the plurality of different types of cells into the other hydrophobic cell culture container or the other cell culture container coated with the hydrophobic material on the bottom thereof to make the plurality of different types of cells to form a plurality of layers; and (d) culturing the plurality of different types of cells to make the plurality of different types of cells connect to each other to form a multilevel structure.

The invention further provides a method for mixing and culturing cells, comprising: (a) culturing a plurality of different types of cells by the method claimed in claim 1, respectively, wherein the plurality of different types of cells attach to the respective carriers; (b) providing another hydrophobic cell culture container or another cell culture container coated with a hydrophobic material on a bottom thereof; (c) mixing the plurality of different types of cells and adding the plurality of different types of cells into the other hydrophobic cell culture container or the other cell culture container coated with the hydrophobic material on the bottom thereof; and (d) culturing the plurality of different types of cells.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
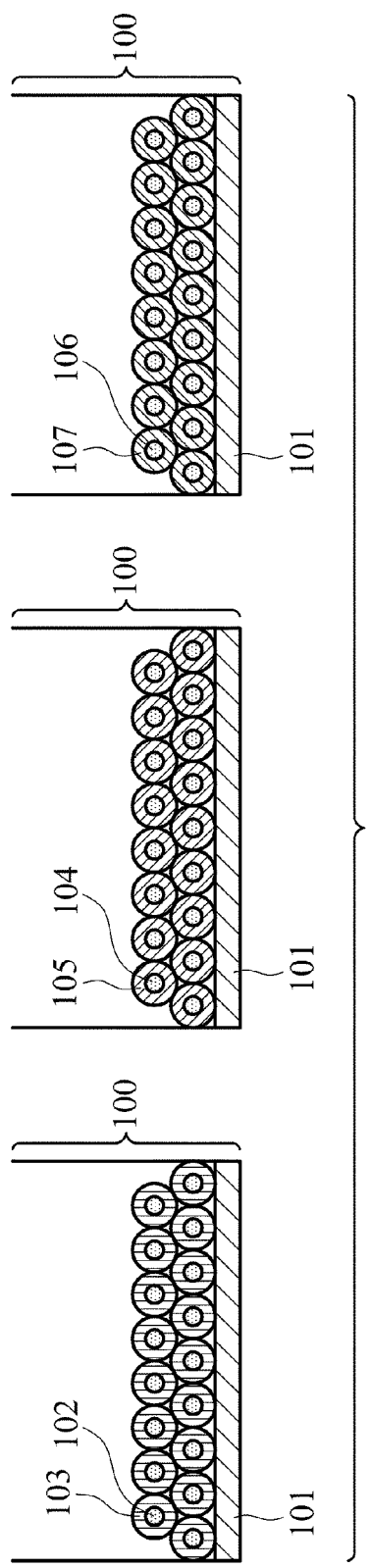
FIGS. 1A-1C show an illustration of the method for culturing cells by stacking cells layer by layer of the invention.

The following description is of the best-contemplated mode of carrying out the invention. This description is made for the purpose of illustrating the general principles of the invention and should not be taken in a limiting sense. The scope of the invention is best determined by reference to the appended claims.

The invention increases the efficiency for cells to attach to the carriers by changing the property of the material of the cell culture container and without chemically modifying the surface of the carriers. Because the cell culture container may be plastic, the invention lowers costs and simplifies the process for cells to be transferred to carriers.

In the method for transferring cells to carriers of the invention, first, a hydrophobic cell culture container is provided. In one embodiment, a material of the hydrophobic cell culture container may comprise silica gel material (such as polydimethylsiloxane (PDMS)), polyethylene (PE), polypropylene (PP), photoresist (such as SU-8 (Micro. Chem.)), polyvinylchloride (PVC), Teflon, polyethylene terephthalate (PET) or polycaprolactone (PCL). Alternatively, a common cell culture container may be coated with a hydrophobic material on the bottom thereof to make the cell culture container be hydrophobic and the hydrophobic material may comprise silica gel material (such as polydimethylsiloxane (PDMS)), polyethylene (PE), polypropylene (PP), photoresist (such as SU-8 (Micro. Chem.)), polyvinylchloride (PVC), Teflon, polyethylene terephthalate (PET) or polycaprolactone (PCL).

Next, carriers which are more hydrophilic than the hydrophobic cell culture container or hydrophobic materials and a culture medium containing cells are added into the hydrophobic cell culture container or the cell culture container coated with the hydrophobic material on the bottom thereof. For example, in one embodiment, when the hydrophobic material is polydimethylsiloxane, the carriers may be gelatin, because compared with polydimethylsiloxane, gelatin is more hydrophilic. In other words, the carriers are not absolutely hydrophilic. The material of the carrier which is more hydrophilic than the hydrophobic cell culture container or the hydrophobic material may comprise chitosan, gelatin, collagen, hyaluronic acid, alginate, polylactic acid or the polymer thereof, polycaprolactone or the polymer thereof, polyanhydrides, poly(amino acid) or polyorthoesters, preferably, gelatin. In one embodiment, the carriers mentioned above may be hydrophilic carriers. Moreover, the shape of the carriers mentioned above may comprise a sheet shape, a granular shape, a bar shape, a sponge shape, a sphere shape, a flat shape or a three-dimensional shape. Furthermore, the carriers may contain a chemical substance or a drug inside thereof, which may be released during culturing of cells. Alternatively, the carriers may be a biodegradable material, such as polylactic acid.

The cells mentioned above may comprise adherent cells, and in one embodiment, the adherent cells may comprise stem cells, endothelium cells, mesenchymal stem cells, cardiomyocytes, smooth muscle cells and fibroblast, preferably, endothelium cells.

Then, the cells are cultured, and during culturing of the cells, due to the hydrophobicity of the cell culture container, the cells do not attach to the cell culture container while attaching to the carriers which are more hydrophilic than the hydrophobic cell culture container or the hydrophobic material. In one embodiment, the carriers are sphere shape, and because the cells attached to the sphere carriers continually grow forming a cell-carrier construct to make the sphere carriers connect to each other, the cell-carrier construct form a multilevel structure or a three-dimensional structure. In the traditional method, in order to make a cell attach to a carrier, the carrier needs to be chemically modified or during the cell culturing process, other processes are needed. For the method of the invention, without chemically modifying the carriers or other processes, the cell may spontaneously attach to the carrier.

Furthermore, the method for transferring cells to carriers mentioned above may be applied in other cell culturing methods.

Figure 1B:
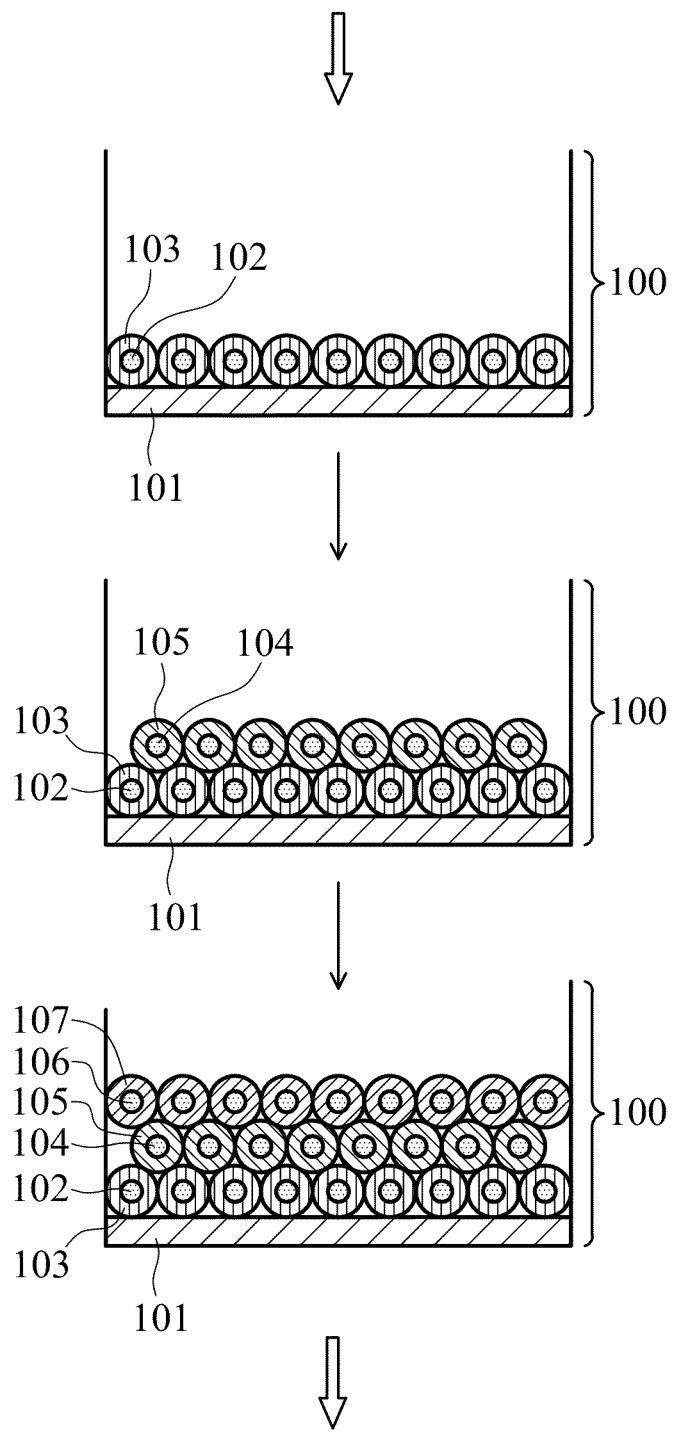
Figure 1C:
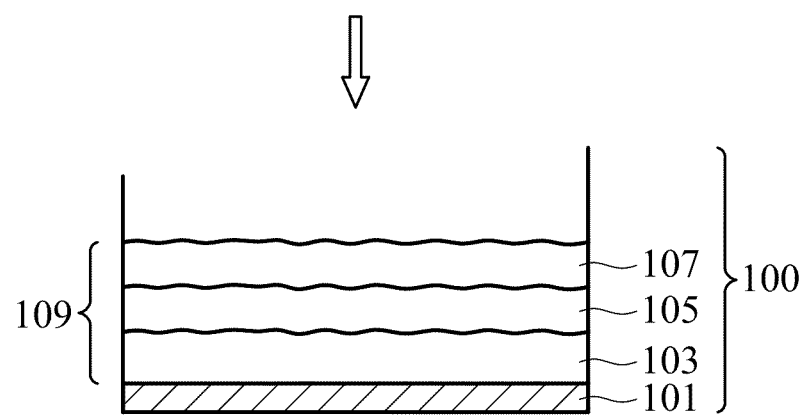

The method for transferring cells to carriers of the invention may be applied in a method for culturing cells by stacking cells layer by layer and an illustration of this method is shown in FIGS. 1A-1C. First, a plurality of different types of cells is cultured by the method for transferring cells to carriers mentioned above, respectively, i.e. different types of cells are not cultured together. As shown in FIG. 1A, symbol 100 represents a cell culture container, symbol 101 represents a hydrophobic material, and symbol 102, 104, and 106 represents carriers which are more hydrophilic than the hydrophobic material 101 (hydrophilic carriers 102, 104 and 106 for short in the following). The material and shape of the hydrophilic carriers 102, hydrophilic carriers 104 and hydrophilic carriers 106 may be the same or different. In addition, symbol 103, 105, and 107 represent different types of cells, respectively and the plurality of the different types of cells 103, 105 and 107 attach to the hydrophilic carriers 102, 104 and 106, respectively.

Next, as FIG. 1B shown, another hydrophobic cell culture container (or a cell culture container coated with a hydrophobic material on a bottom thereof) 100 mentioned above is provided. Then, the different types of cells attached on the respective hydrophilic carriers are added in the other hydrophobic cell culture container (or a cell culture container coated with a hydrophobic material on a bottom thereof) to make the plurality of different types of cells form a plurality of layers, wherein the plurality of different types of cells are continually cultured. Because the cells attached on the granular carriers continually grow to make the granular carriers connect to each other, the different types of cells form a multilevel structure or a three-dimensional structure.

In one embodiment, the plurality of different types of cells may comprise a first type of cells, a second type of cells and a third type of cells, and the first type of cells is located at a first layer, the second type of cells is located at a second layer and the third type of cells is located at a third layer.

As shown in FIGS. 1B and 1C, the material of the hydrophilic carriers 102, hydrophilic carriers 104 and hydrophilic carriers 106 may be a biodegradable material which degrades during cell culturing. In one embodiment, the first type of cells is fibroblasts, the second type of cells is epidermal cells and the third type of cells is keratinocytes, and after cell culturing, the first type of cells, the second type of cells and the third type of cells become a skin tissue structure 109. In other embodiment, the first type of cells is limbal stem cells, the second type of cells is fibroblasts and the third type of cells is epithelial cells, and after cell culturing the first type of cells, the second type of cells and the third type of cells become a limbal tissue structure 109. In further other embodiment, the first type of cells is cardiomyocytes, the second type of cells is stem cells and the third type of cells is endothelial cells, and after cell culturing, the first type of the cells, the second type of cells and the third type of cells become a cardiac tissue structure.

Figure 2:
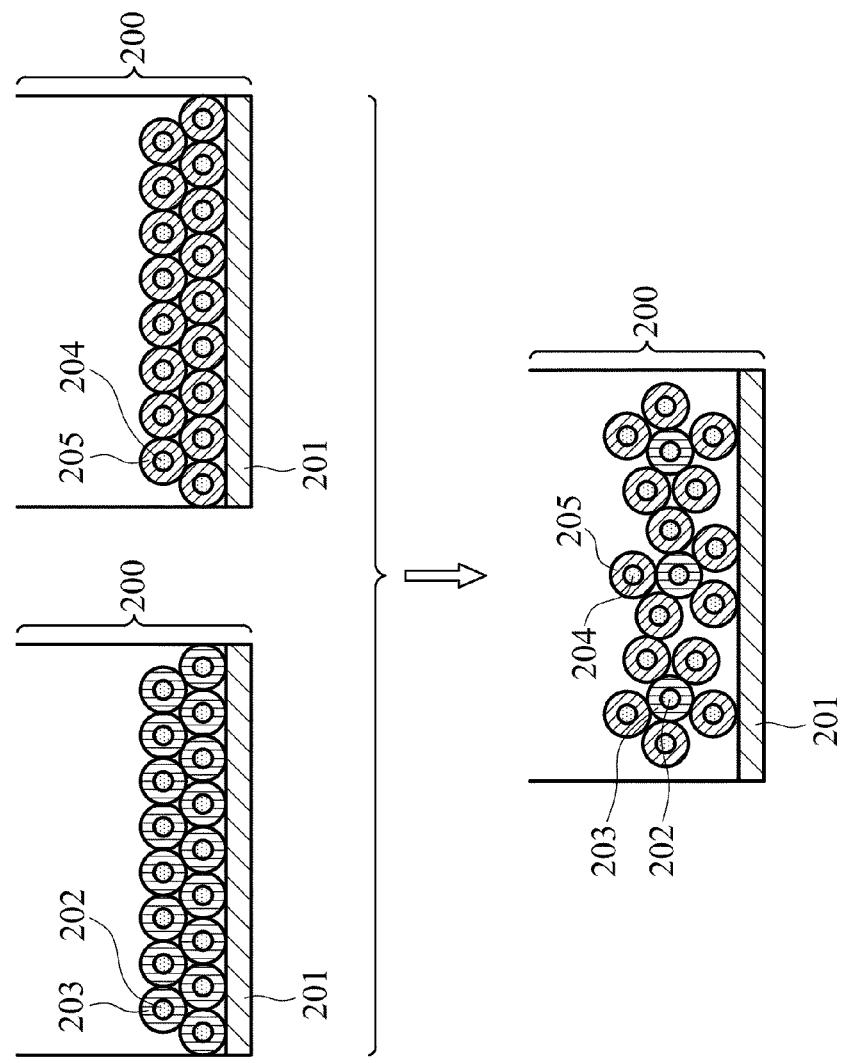
FIG. 2 shows an illustration of the method for mixing and culturing cells of the invention.

Moreover, the method for transferring cells to carriers of the invention may be applied in a method for mixing and culturing cells, and an illustration of this method is shown in FIG. 2. First, a plurality of different types of cells is cultured by the method for transferring cells to carriers mentioned above, respectively, i.e. different types of cells are not cultured together. As the upper part of FIG. 2 shows, symbol 200 represents a cell culture container, symbol 201 represents a hydrophobic material, and symbol 202 and 204 represents carriers which are more hydrophilic than the hydrophobic material 201 (hydrophilic carriers 202 and 204 for short in the following). The material and shape of the hydrophilic carriers 202 and hydrophilic carriers 204 may be the same or different. In addition, symbols 203 and 205 represent different types of cells, respectively and the plurality of different types of cells 203 and 205 attach to the hydrophilic carriers 202 and 204, respectively.

Following, as the lower part of FIG. 2 shows, another hydrophobic cell culture container (or a cell culture container is coated with a hydrophobic material on a bottom thereof) 200 mentioned above is provided. Then, the different types of cells attached on respective hydrophilic carriers are mixed and added in the other hydrophobic cell culture container (or a cell culture container coated with a hydrophobic material on a bottom thereof). The plurality of different types of cells may be mixed by a ratio.

The plurality of different types of cells may comprise a first type of cells and a second type of cells. In one embodiment, the first type of cells is stem cells and the second type of cells is nerve cells and a mixing ratio of the stem cells to the nerve cells is about 100:1-1:100. In other embodiment, the first type of cells is stem cells and the second type of cells is chondrocytes. In further other embodiment, the first type of cells is hair follicle stem cells and the second type of cells is epithelial cells.

EXAMPLE

Comparative Example 1

Figure 3:
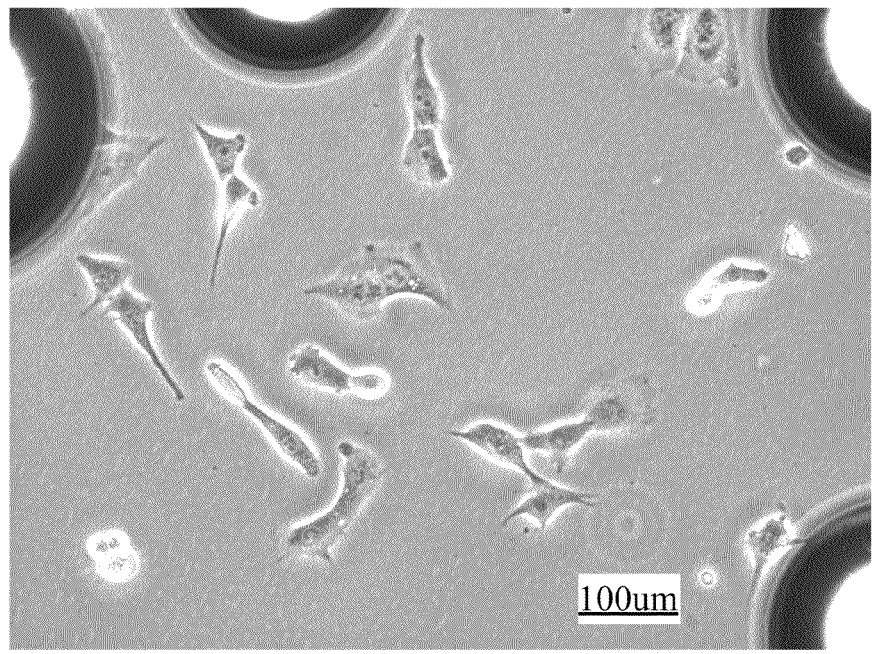
FIG. 3 shows the result for culturing fibroblasts with a commercial culturing plate.

Culturing Cells with a Culturing Plate Made of a Non-hydrophobic Material 0.5 ml of fibroblasts ($10^5$ cell/ml) was added in a culturing plate (CORNING®) with 3 cm in diameter made of polystyrene and then, 1.5 ml of DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 1 day, the culturing plate was photographed by an inverted microscope (Olympus IX70) and the result is shown in FIG. 3. FIG. 3 shows the result for culturing fibroblasts with a culturing plate made of polystyrene (40×). As FIG. 3 shows, fibroblasts are attached on the bottom of the culturing plate.

Comparative Example 2

Figure 4:
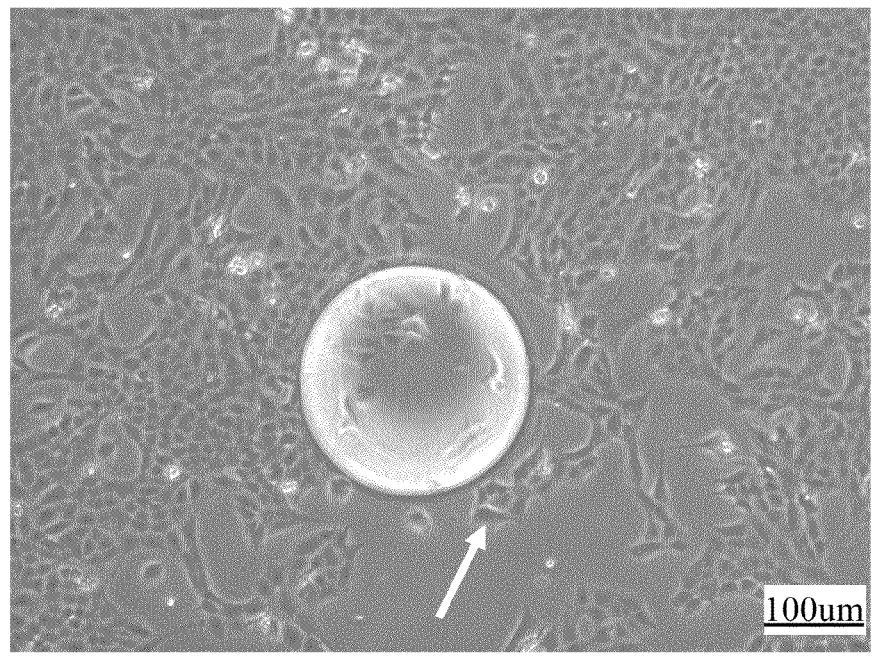
FIG. 4 shows the result for culturing cells with a commercial culturing plate and gelatin microspheres.

Culturing Cells with a Culturing Plate Made of a Non-hydrophobic Material and Gelatin Microspheres An appropriate mount of gelatin microspheres were flatly applied in a 6-well culturing plate (CELLSTAR®). Then, 0.5 ml of fibroblasts ($8\times10^5$ cell/ml) was added in the culturing plate. 1.5 ml of DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 1 day, the culturing plate was photographed by an inverted microscope (Olympus IX70) and the result is shown in FIG. 4. FIG. 4 shows the result for culturing fibroblasts with a culturing plate made of polystyrene and gelatin microspheres (40×), wherein the spheres are gelatin microspheres and the position pointed out by the arrow of FIG. 4 is cells. As FIG. 4 shows, most of the fibroblasts are attached on the bottom of the culturing plate and not to the gelatin microspheres.

Comparative Example 3

Culturing Cells with a Culturing Plate Made of a Non-hydrophobic Material and Chitosan Film 700 μl of 2% chitosan solution was dropped evenly on a cover glass (24×32 $mm^2$). The cover glass was placed in a negative pressure chamber with atmosphere lower than 400 mm-Hg for 24 hours. Next, the cover glass was taken out from the negative pressure chamber and placed in a hood for 24 hours to dry the chitosan solution on the cover glass to form a chitosan film. 0.5 $cm^2$ of the chitosan film was applied in a commercial polystyrene 24-well culturing plate (CELLSTAR®). Then, 1 ml of fibroblasts ($2.5\times10^4$ cell/ml) was added in the culturing plate with the chitosan film. 1.5 ml of DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 2 days and 6 days, the culturing plate was photographed by an inverted microscope (Olympus IX70) at each time point, and the results are shown in FIGS. 5A and 5B, respectively.

Figure 5A:
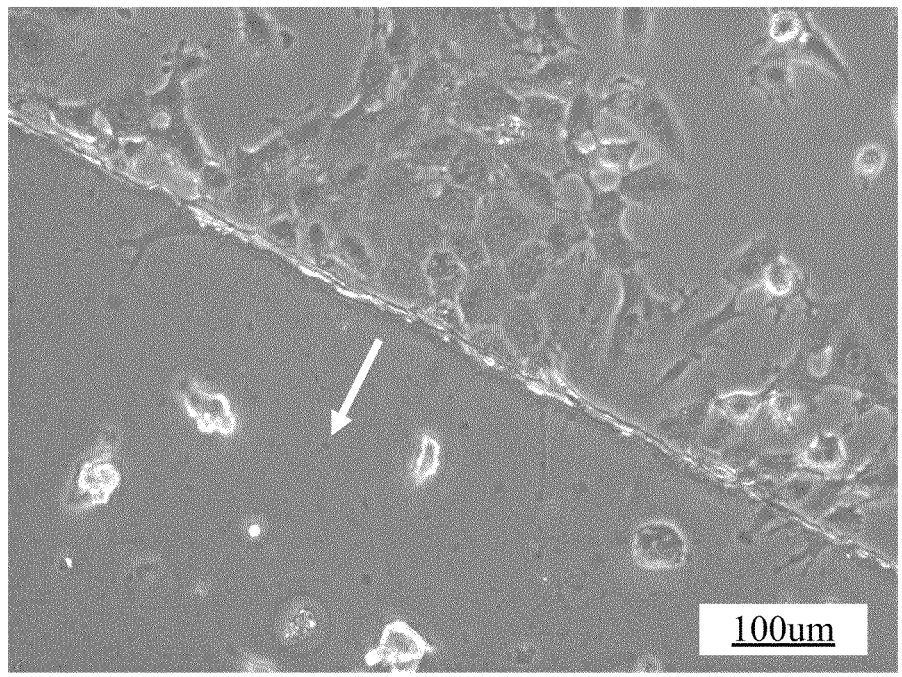
FIGS. 5A and 5B show the result for culturing cells with a commercial culturing plate and a chitosan film.

In FIG. 5A, the position pointed by the arrow is the chitosan film. FIG. 5A shows that most of the cells are attached on the culturing plate not to the chitosan film.

Figure 5B:

In FIG. 5B, the position pointed by the arrow is the chitosan film. Compared with FIG. 5A, in FIG. 5B, the total number of the cells is greater; however most of the cells are still attached on the culturing plate and not to the chitosan film. Furthermore, the edges of the chitosan film were clear, which means that the cells did not grow from the polystyrene culturing plate to the chitosan film.

Example 1

Culturing Cells with a Culturing Plate Coated with Polydimethylsiloxane (Hydrophobic Material) on the Bottom Thereof and Glass Beads The air in a polydimethylsiloxane (PDMS) solution (DOW CORING SYLGARD® 184) was removed by a vacuum drying machine. Then, an appropriate mount of polydimethylsiloxane solution was added into a 6-well culturing plate (CELLSTAR®) and kept in the culturing plate over a night time period to harden the polydimethylsiloxane completely (heating at 60° C. is able to accelerate the polydimethylsiloxane being hardened on the culturing plate). Next, an appropriate mount of glass beads were applied in the 6-well culturing plate coated with polydimethylsiloxane on the surface thereof. 0.5 ml of fibroblasts ($10^5$ cell/ml) was added in the 6-well culturing plate coated with polydimethylsiloxane on the surface thereof. 1.5 ml of DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 5 days, the culturing plate was photographed by an inverted microscope (Olympus IX70). The results magnified by 40× and 60× are shown in FIGS. 6A and 6B, respectively.

Figure 6A:
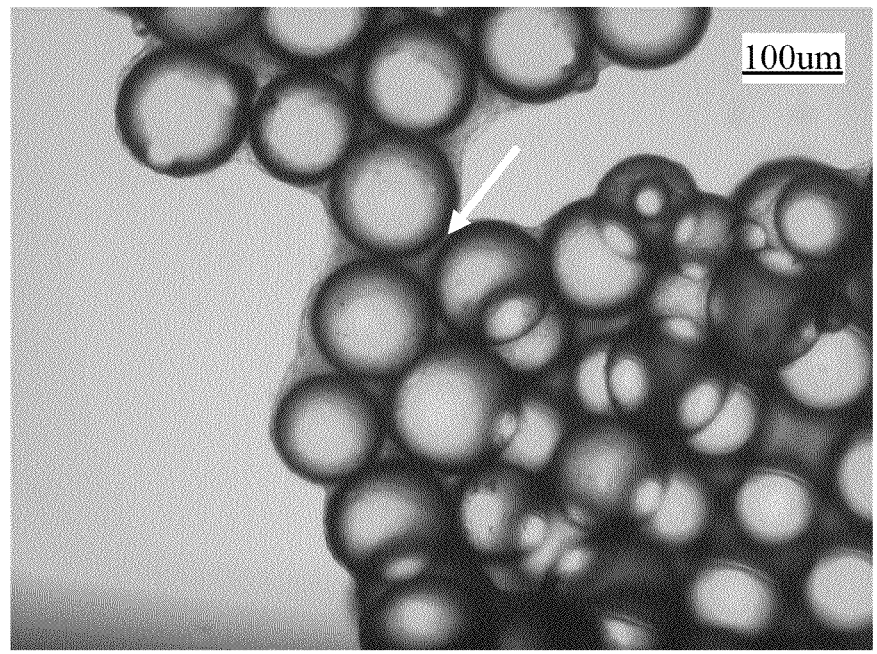
FIGS. 6A and 6B show the results for culturing cells with a culturing plate coated with polydimethylsiloxane on the bottom thereof and glass beads.

In FIG. 6A, the position pointed out by the arrow is a fibroblast. As FIG. 6A shows, the sphere frameworks were fully covered by the cells. The cells not only attached on the sphere frameworks but also connected the sphere frameworks to each other to form a multilevel structure.

Figure 6B:
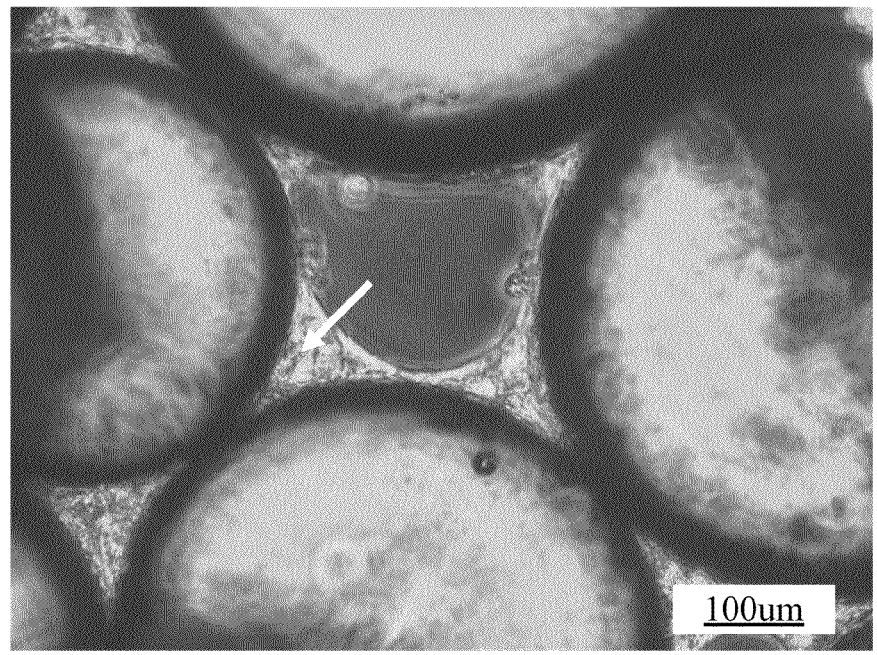

In FIG. 6B, the position pointed out by the arrow is a fibroblast. As FIG. 6B shows, the sphere frameworks were fully covered by the cells. The cells formed connections among the sphere frameworks to maintain the configuration formed by the sphere frameworks.

Example 2

Culturing Cells with a Culturing Plate Coated with Polydimethylsiloxane (Hydrophobic Material) on the Bottom Thereof and Gelatin Microspheres The air in a polydimethylsiloxane (PDMS) solution (DOW CORING SYLGARD® 184) was removed by a vacuum drying machine. Then, an appropriate mount of polydimethylsiloxane solution was added into a 6-well culturing plate (CELLSTAR®) and kept in the culturing plate over a night time period to harden the polydimethylsiloxane completely (heating at 60° C. is able to accelerate the polydimethylsiloxane harden on the culturing plate). Next, an appropriate mount of gelatin microspheres were applied in the 6-well culturing plate coated with polydimethylsiloxane on the surface thereof. 0.5 ml of fibroblasts ($8 \times 10^5$ cell/ml) was added in the 6-well culturing plate coated with polydimethylsiloxane on the surface thereof. 1.5 ml of DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 4 days, 10 days 15 days and 19 days, the culturing plate was photographed by an inverted microscope (Olympus IX70) at each time point and the results are shown in FIGS. 7A-D, respectively.

Figure 7A:
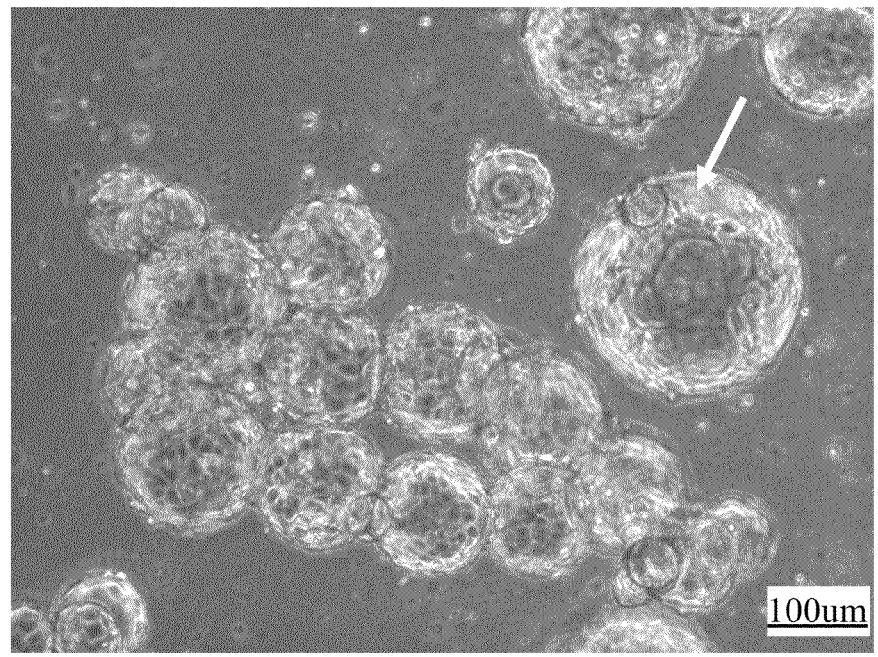
FIGS. 7A-7D show the results for culturing cells with a culturing plate coated with polydimethylsiloxane on the bottom thereof and gelatin microspheres.
Figure 7B:
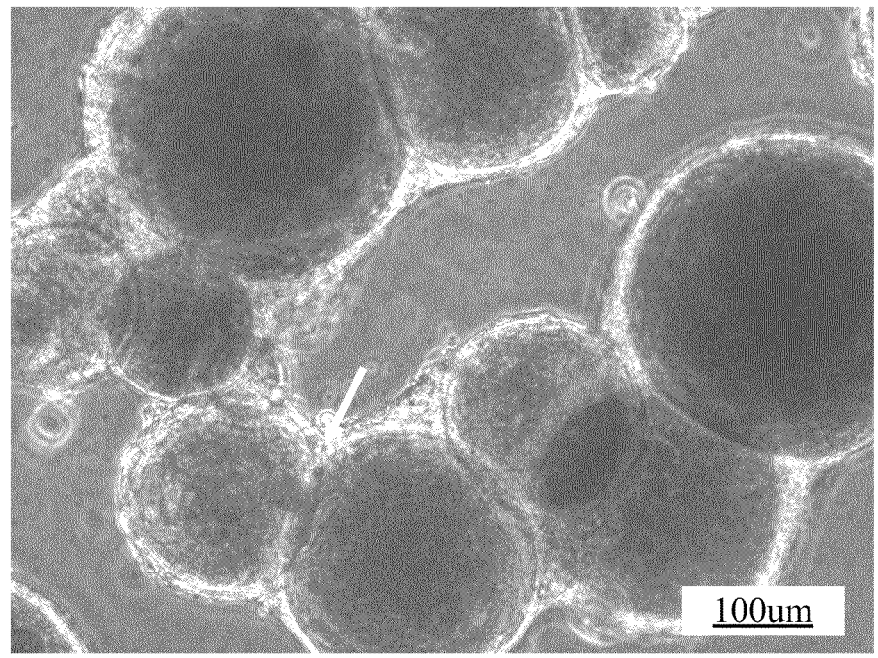
Figure 7C:
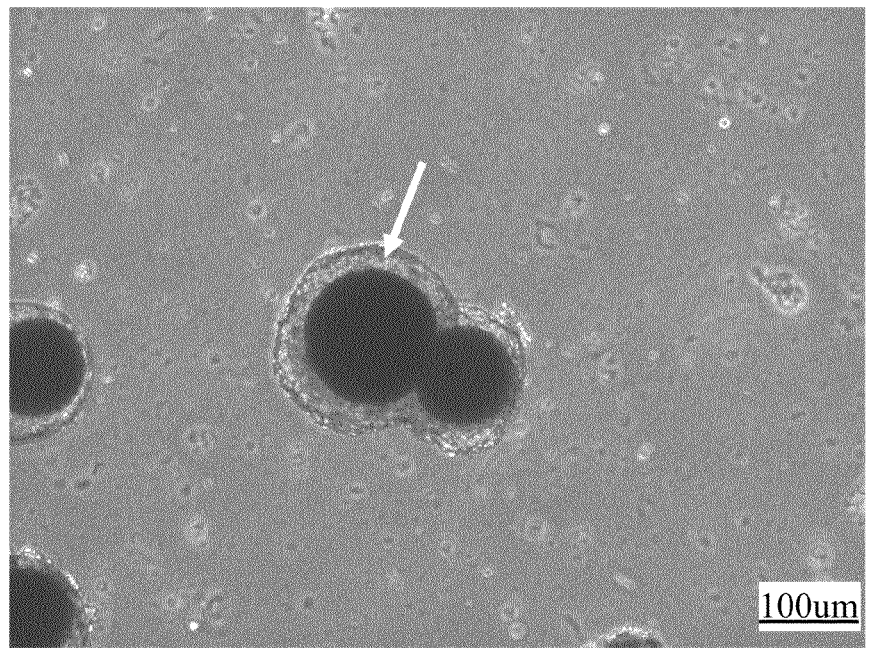
Figure 7D:
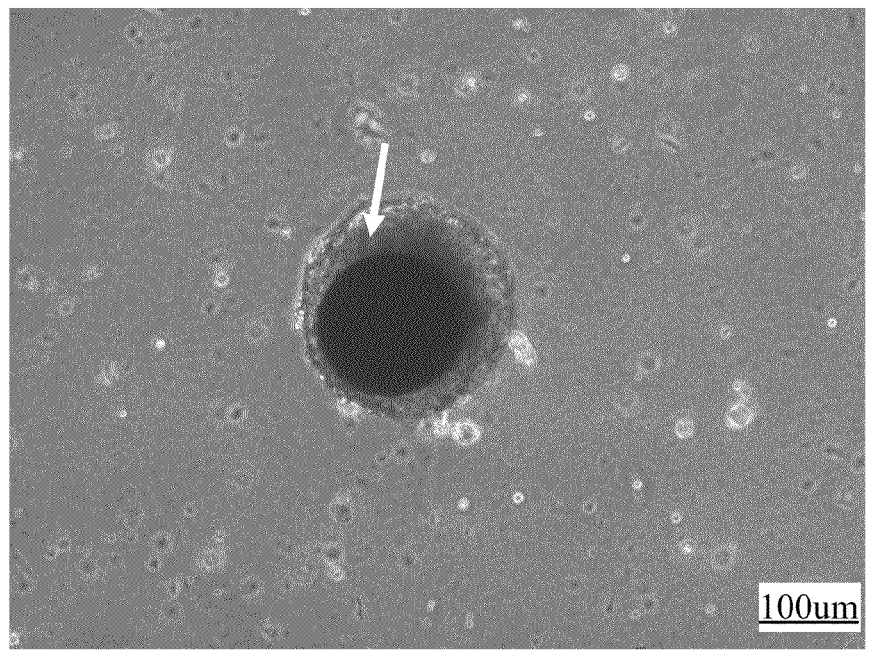

In FIGS. 7A-7D, the spheres are transparent gelatin microspheres and the position pointed out by the arrow is a cell. As shown in FIGS. 7A-7D, the transparent gelatin microspheres were fully covered by cells while there were no apparent cells attached on the polydimethylsiloxane substrate. This revealed that under the polydimethylsiloxane system, the cells were able to attach to the three-dimensional materials successfully. Furthermore, FIGS. 7C and 7D show that after a long period of culturing, the transparent gelatin microspheres were surrounded by the cells and cell-carrier construct were formed.

Example 3

Culturing Cells with a Culturing Plate Coated with Polydimethylsiloxane (Hydrophobic Material) on the Bottom Thereof and a Chitosan Film 700 µl of 2% chitosan solution was dropped evenly on a cover glass (24×32 mm²). The cover glass was placed in a negative pressure chamber with atmosphere lower than 400 mm-Hg for 24 hours. Next, the cover glass was taken out from the negative pressure chamber and placed in a hood for 24 hours to dry the chitosan solution on the cover glass to form a chitosan film.

Figure 8A:
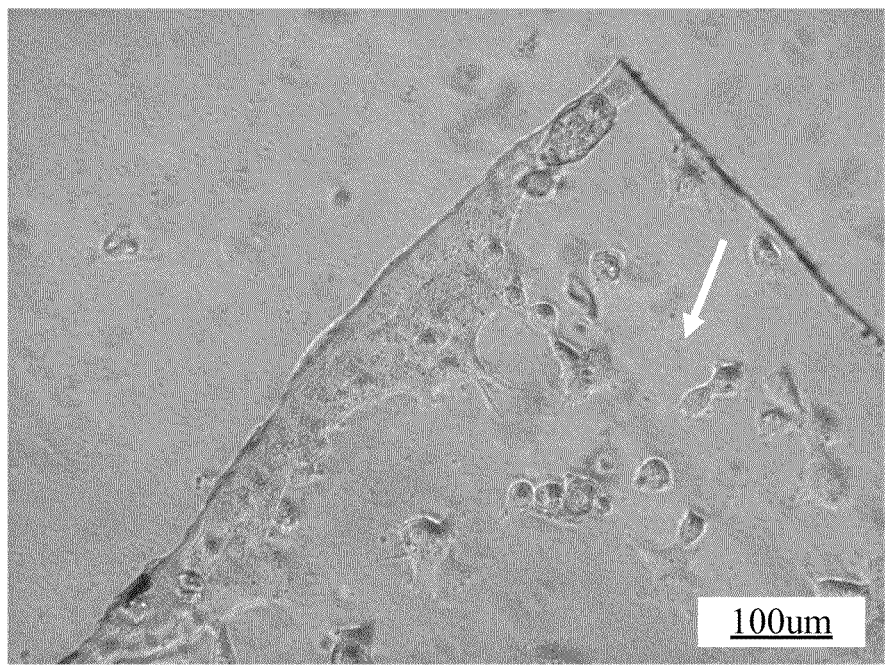
FIGS. 8A and 8B show the 2-day results for culturing cells with a culturing plate coated with polydimethylsiloxane on the bottom thereof and a chitosan film.
Figure 8B:
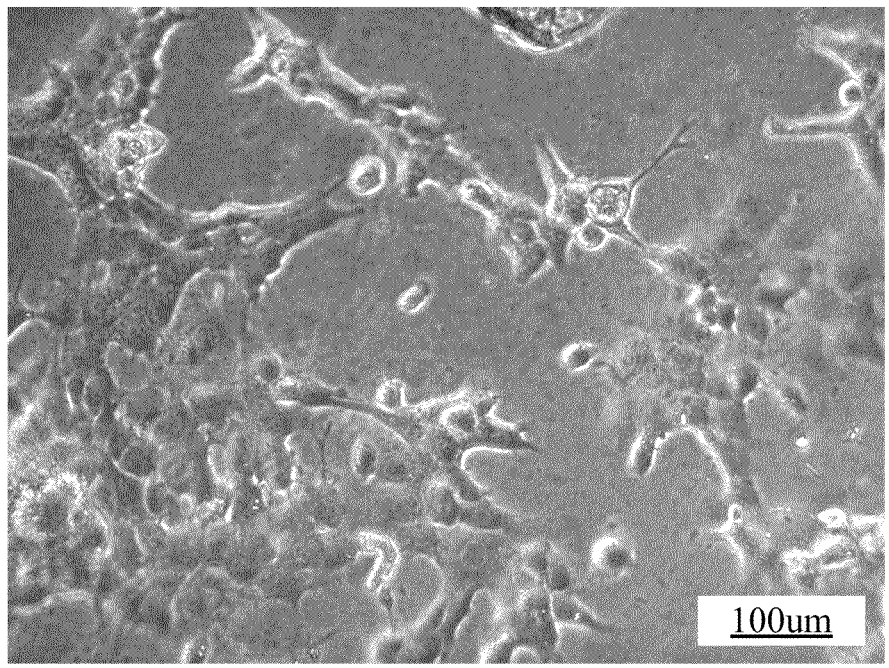

The air in a polydimethylsiloxane (PDMS) solution (DOW CORING SYLGARD® 184) was removed by a vacuum drying machine. Then, an appropriate mount of polydimethylsiloxane solution was added into a 24-well culturing plate (CELLSTAR®) and kept in the culturing plate over a night time period to harden the polydimethylsiloxane completely (heating at 60° C. is able to accelerate the polydimethylsiloxane being hardened on the culturing plate). Next, 0.5 cm² of the chitosan film was applied in the 24-well culturing plate coated with polydimethylsiloxane on the surface thereof. 1 ml of fibroblasts ($2.5 \times 10^4$ cell/ml) was added in the 24-well culturing plate coated with polydimethylsiloxane on the surface thereof. DMEM (Dulbecco's Modified Eagle Medium, GIBCO®) containing 10% FBS (fetal bovine serum, GIBCO®) was added into the culturing plate. After that, the culturing plate with fibroblasts was placed in a cell culture incubator (REVCO®) (37° C.; 5% $CO_2$) for cell culturing. After culturing for 2 days and 6 days, the culturing plate was photographed by an inverted microscope (Olympus IX70) at each time point and the results were shown in FIGS. 8A, 8B and 9A, 9B, respectively. FIGS. 8A and 8B show the 2-day results for cell culturing with a culturing plate coated with polydimethylsiloxane on the bottom thereof and chitosan film.

As shown in FIG. 8A, the position pointed out by the arrow is the chitosan film and most of the cells are attached to the chitosan film. FIG. 8B shows the condition of the cells on the chitosan film. As shown in FIG. 8B, the condition for the cells attaching on the chitosan film was appropriate and this revealed that the cells were able to attach on the chitosan film and proliferate, successfully.

Figure 9A:
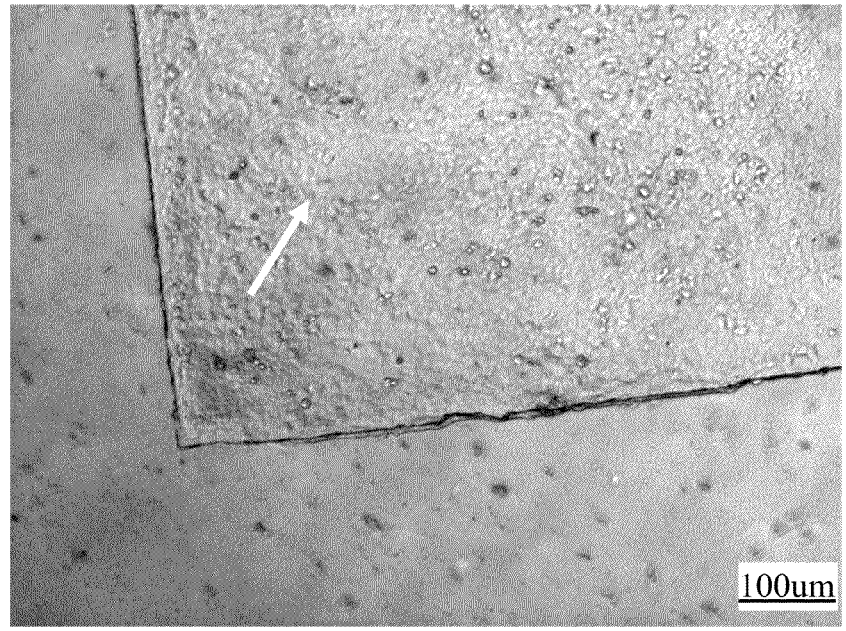
FIGS. 9A and 9B show the 6-day results for culturing cells with a culturing plate coated with polydimethylsiloxane on the bottom thereof and a chitosan film.
Figure 9B:
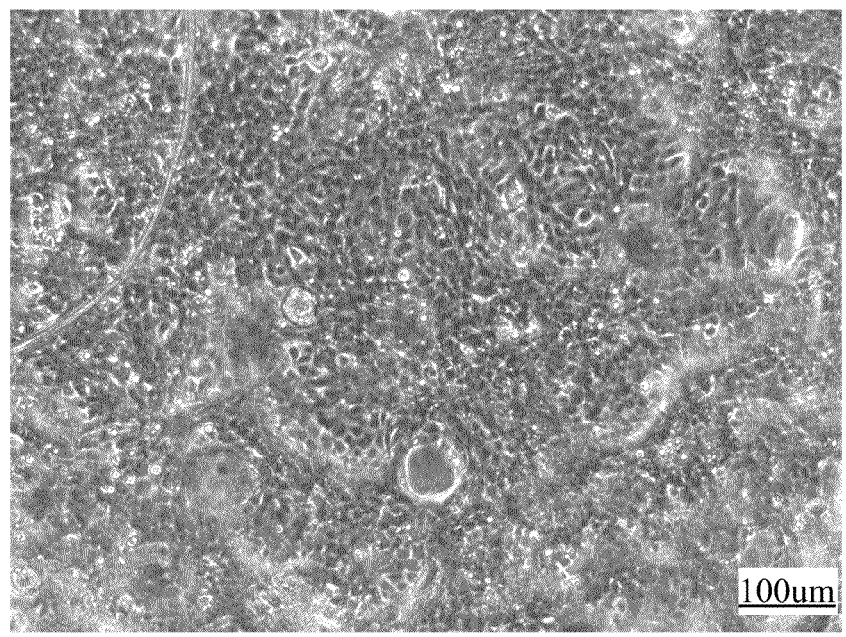

FIGS. 9A and 9B show the 6-day results for cell culturing with a culturing plate coated with polydimethylsiloxane on the bottom thereof and a chitosan film. As shown in FIG. 9A, the position pointed out by the arrow is the chitosan film and the cells almost completely covered the chitosan film. In addition, the edges of the chitosan film were clear and this showed that the cell did not grow beyond the chitosan film. FIG. 9B shows the condition of the cells on the chitosan film. As shown in FIG. 9B, the condition for the cells attaching on the chitosan film was appropriate and this revealed that the cells were able to attach on the chitosan film and proliferate, successfully.

Example 4

Culturing Cells with a Culturing Plate Coated with Polyvinylchloride (Hydrophobic Material) on the Bottom Thereof and Gelatin Microspheres A commercial polyvinylchloride cling film (NANYA Plastics Corporation) was cut in a circle with 3.3 cm in diameter and applied in a commercial 6-well culturing plate. Then, an acrylic ring with 0.5 cm in thickness, 3.0 cm in inside diameter and 3.3 cm in outer diameter was used to press down the polyvinylchloride cling film to prevent floating. Next, an appropriate mount of gelatin microspheres were applied on the polyvinylchloride cling film in the 6-well culturing plate. 1 ml of GFP fibroblasts ($2.5 \times 10^4$ cell/ml) was added in the 6-well culturing plate with polyvinylchloride cling film. The culturing plate with GFP fibroblasts was placed in a cell culture incubator (REVCO®) (37° C.; 5% $CO_2$) for cell culturing. After culturing for 1 day and 3 days, the culturing plate was photographed by an inverted microscope (Olympus IX70) at each time point and the results were shown in FIGS. 10A and 10B, respectively.

Figure 10A:
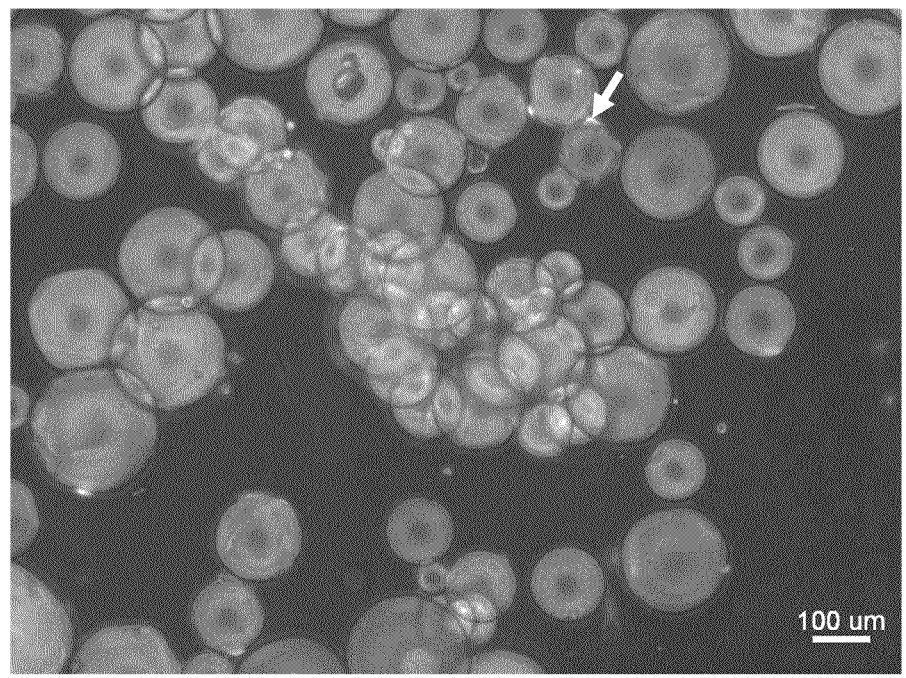
FIGS. 10A and 10B show the results for culturing cells with a culturing plate with polyvinylchloride on the bottom thereof and gelatin microspheres.
Figure 10B:
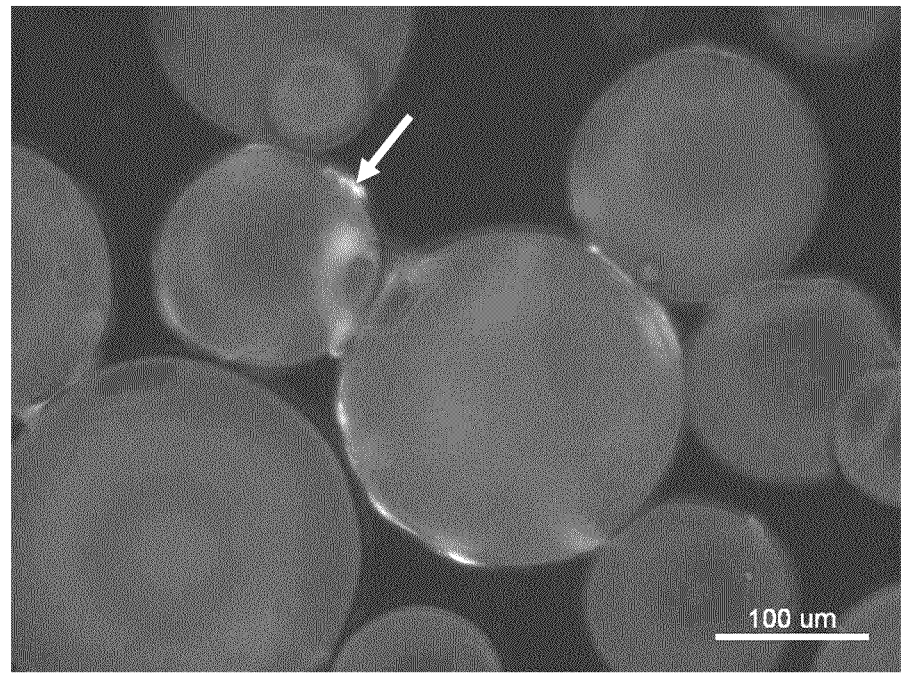

In FIGS. 10A and 10B, the position pointed out by the arrow is the GFP fibroblasts and the spheres were gelatin microspheres. As shown in 10A and 10B, the cells are attached on the gelatin microspheres framework not other positions.

Example 5

Culturing Cells with a Culturing Plate with a Polydimethylsiloxane Ring and Gelatin Microspheres The air in a polydimethylsiloxane (PDMS) solution (DOW CORING SYLGARD® 184) was removed by a vacuum drying machine. Then, an appropriate mount of polydimethylsiloxane solution was added into a 6-well culturing plate (CELLSTAR®) and kept in the culturing plate over a night time period to harden the polydimethylsiloxane completely (heating at 60° C. is able to accelerate the polydimethylsiloxane being hardened on the culturing plate). An appropriate mount of gelatin microspheres were applied in the 6-well culturing plate coated with polydimethylsiloxane on the surface thereof. 0.5 ml of GFP fibroblasts ($8 \times 10^5$ cell/ml) was added in the 6-well culturing plate coated with polydimethylsiloxane on the surface thereof. 1.5 ml of DMEM (Dulbecco's Modified Eagle Medium, GIBCO®) containing 10% FBS (fetal bovine serum, GIBCO®) was added into the culturing plate. After that, the culturing plate with GFP fibroblasts was placed in a cell culture incubator (REVCO®) (37° C.; 5% $CO_2$) for cell culturing.

After culturing for 3 days, the gelatin microspheres attached by the cells were removed into a circle fillister made of a hydrophobic material (PDMS) and placed in the cell culture incubator (REVCO®) (37° C.; 5% $CO_2$) for culturing. After 1 hour, 4 ml of DMEM was added into the circle fillister and the circle fillister with GFP fibroblasts was cultured in the cell culture incubator (REVCO®) (37° C.; 5% $CO_2$). After culturing for 3 days, the circle fillister was photographed by a common camera and an inverted microscope (Olympus IX70) and the results were shown in FIGS. 11A and 11B, respectively.

Figure 11A:
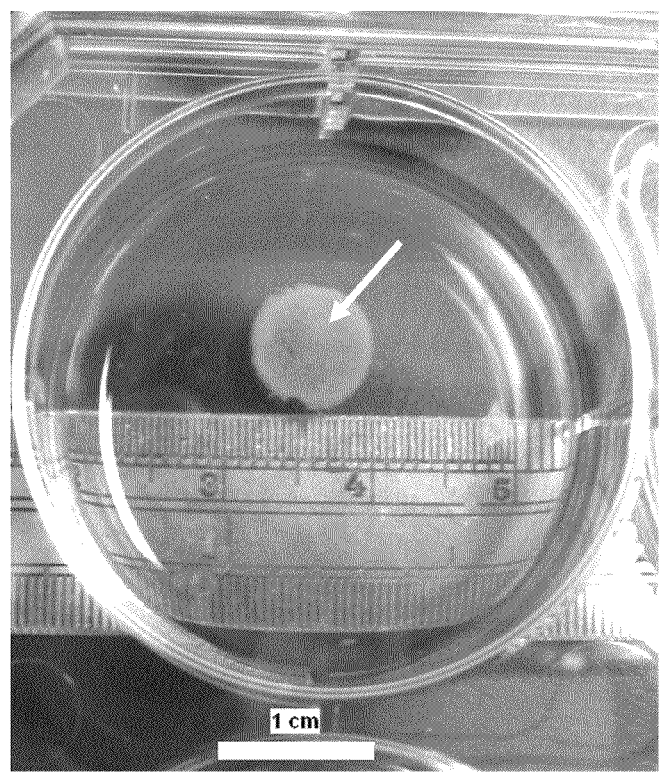
FIGS. 11A and 11B show the results for culturing cells with a culturing plate with a polydimethylsiloxane ring and gelatin microspheres.
Figure 11B:
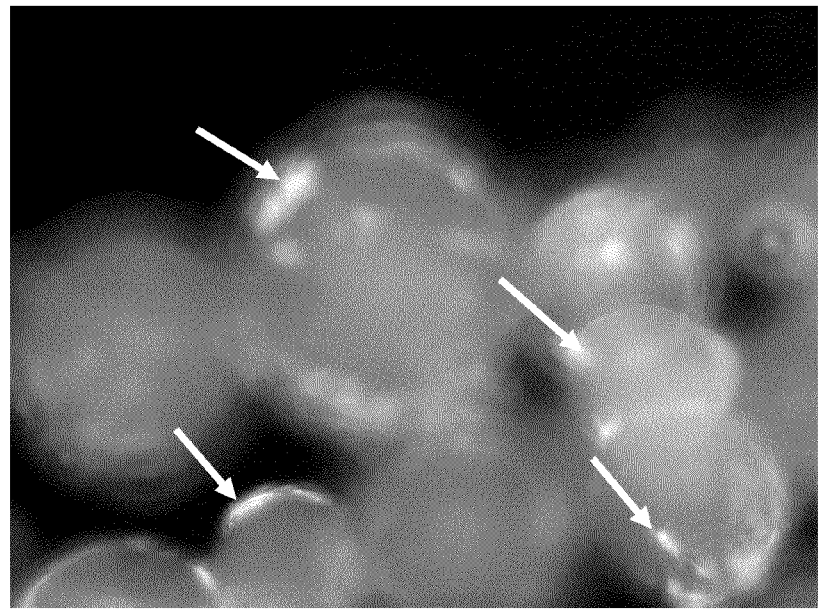

In FIG. 11A, the position pointed out by the arrow is gelatin microspheres and the cell-carrier construct. As shown in FIG. 11A, the cells attaching on the gelatin microspheres were able to connect the gelatin microspheres to each other and the growth of the cell-carrier construct was limited by the shape of the circle fillister made of PDMS and thus the cell-carrier construct formed the shape of the cylinder and maintained the shape successfully. This showed that the cells successfully played a role as a bridge to compactly connect the gelatin microspheres. In FIG. 11B, the positions pointed out by the arrows are the cells. As shown in FIG. 11B, the cells are attached on the gelatin microspheres and grew.

Example 6

Culturing Different Types of Cells Layer by Layer

The air in a polydimethylsiloxane (PDMS) solution (DOW CORING SYLGARD® 184) was removed by a vacuum drying machine. Then, an appropriate mount of polydimethylsiloxane solution was added into a 6-well culturing plate (CELLSTAR®) and kept in the culturing plate over a night time period to harden the polydimethylsiloxane completely (heating at 60° C. is able to accelerate the polydimethylsiloxane being hardened on the culturing plate). An appropriate mount of gelatin microspheres were applied in the 6-well culturing plate coated with polydimethylsiloxane on the surface thereof. 0.5 ml of cardiomyocytes ($8 \times 10^5$ cell/ml) was added in the 6-well culturing plate coated with polydimethylsiloxane on the surface thereof. 1.5 ml of medium 199 (GIBCO®) was added into the culturing plate. After that, the culturing plate with cardiomyocytes was placed in a cell culture incubator (REVCO®) (37° C.; 5% $CO_2$) for cell culturing.

After culturing for 3 days, the gelatin microspheres attached by the cardiomyocytes were removed into a circle fillister made of a hydrophobic material (PDMS) and placed in the cell culture incubator (REVCO®) (37° C.; 5% $CO_2$) for culturing. After 1 hour, 4 ml of medium 199 (GIBCO®) was added into the circle fillister and the circle fillister with cardiomyocytes was cultured in the cell culture incubator (REVCO®) (37° C.; 5% $CO_2$). After culturing for 3 days, the circle fillister was photographed by a common camera and an inverted microscope (Olympus IX70).

An appropriate mount of gelatin microspheres were applied in a 6-well culturing plate coated with polydimethylsiloxane on the surface thereof. 0.5 ml of mesenchymal stem cells ($8 \times 10^5$ cell/ml) was added in the 6-well culturing plate coated with polydimethylsiloxane on the surface thereof. 1.5 ml of Alpha MEM medium (Minium Essential Medium, GIBCO®) was added into the culturing plate. After that, the culturing plate with mesenchymal stem cells was placed in a cell culture incubator (REVCO®) (37° C.; 5% $CO_2$) for cell culturing. After culturing for 3 days, the gelatin microspheres attached by the mesenchymal stem cells were removed into the circle fillister with the cardiomyocytes mentioned above and placed in the cell culture incubator (REVCO®) (37° C.; 5% $CO_2$) for culturing. After 1 hour, 4 ml of DEME-F12 (Dulbecco's Modified Eagle Medium, GIBCO®) was added into the circle fillister and the circle fillister with cardiomyocytes and mesenchymal stem cells was placed in the cell culture incubator (REVCO®) (37° C.; 5% $CO_2$) for co-culturing the cardiomyocytes and mesenchymal stem cells. After culturing for 3 days, the vertical section view of the circle fillister was photographed by an inverted microscope (Olympus IX70) and the result is shown in FIG. 12.

Figure 12:
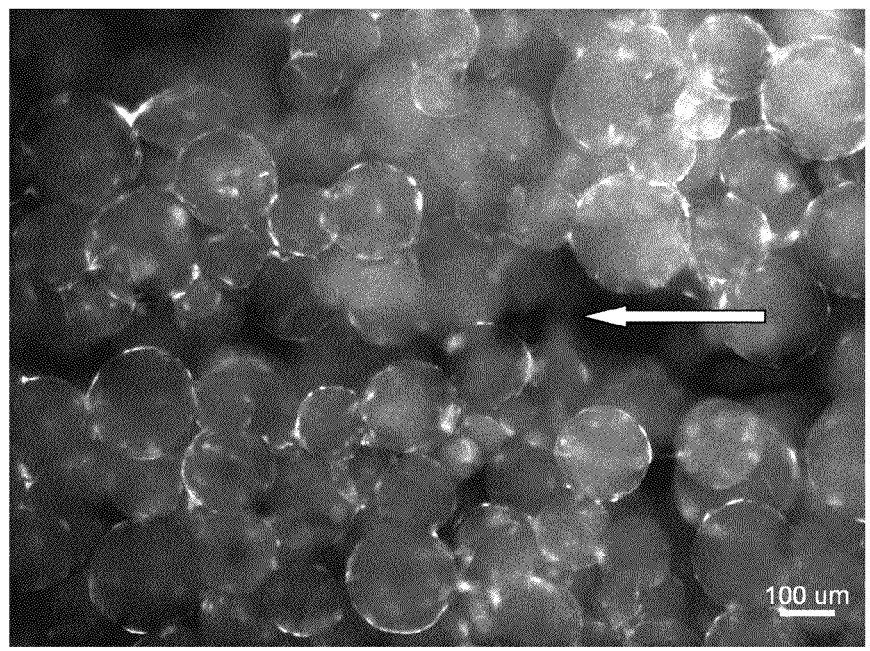
FIG. 12 shows the result for culturing different types of cells layer by layer.

As shown in FIG. 12, the cells attaching to the gelatin microspheres were able to connect the gelatin microspheres to each other and the growth of the cell-carrier construct was limited by the shape of the circle fillister made of PDMS and thus the cell-carrier construct formed the shape of the cylinder and maintained the shape successfully. This showed that the cells successfully played a role as a bridge to compactly connect the gelatin microspheres. The position pointed out by the arrow was the boundary between the two different types of cells. The upper part of the cells was mesenchymal stem cells and the lower part of the cells was the cardiomyocytes. After stacking, the gelatin microspheres attached by the cardiomyocytes and the gelatin microspheres attached by the mesenchymal stem cells formed a double layer structure successfully.

Example 7

Mixing and Culturing Different Types of Cells

The air in a polydimethylsiloxane (PDMS) solution (DOW CORING SYLGARD® 184) was removed by a vacuum drying machine. Then, an appropriate mount of polydimethylsiloxane solution was added into a 6-well culturing plate (CELLSTAR®) and kept in the culturing plate over a night time period to harden the polydimethylsiloxane completely (heating at 60° C. is able to accelerate the polydimethylsiloxane being hardened on the culturing plate). An appropriate mount of gelatin microspheres were applied in the 6-well culturing plate coated with polydimethylsiloxane on the surface thereof. 0.5 ml of cardiomyocytes ($8 \times 10^5$ cell/ml) and 0.5 ml of mesenchymal stem cells ($8 \times 10^5$ cell/ml) were added in the 6-well culturing plate coated with polydimethylsiloxane on the surface thereof. 1 ml of DMEM-F12 (GIBCO®) was added into the culturing plate. After that, the culturing plate with fibroblasts was placed in a cell culture incubator (REVCO®) (37° C.; 5% $CO_2$) for co-culturing the cardiomyocytes and mesenchymal stem cells. After culturing for 6 days, Hoechst33342 (Invitrogen) (blue fluorescence) was used to stain the cell nucleuses of the cells. Anti-troponin antibody (mouse IgG2a anti-rat 1:200, Santa Cruz) as a first antibody was used to bind to the cell skeletons of the cardiomyocytes and then anti-mouse IgG-FITC (donley anti-mouse IgG-FITC sc-2099, Santa Cruz) as a secondary antibody was used to bind to the first antibody to make the cytoplasmas of the cardiomyocytes present green fluorescence. Next, the vertical section view of the cell-carrier construct was photographed by an inverted microscope (Olympus IX70) and the result is shown in FIG. 13.

In addition, the detailed steps for the cell nucleus stain process are described in the following:

The medium in the culturing plate with cells was removed and the culturing plate with cells was washed by a sterilized PBS buffer for three times and then the PBS buffer was removed. 3.7% formaldehyde (Wako, Japan) was added into the culturing plate and kept in the culturing plate for 30 minutes for fixing cells. After fixing, the formaldehyde was removed. Next, 0.1% Triton X-100 (Wako, Japan) was added into the culturing plate and kept in the culturing plate for 5 minutes. Then, 5% fetal bovine serum (FBS) was added into the culturing plate and kept in the culturing plate for 30 minutes and the culturing plate was washed by sterilized PBS buffer for three times. After that, the sterilized PBS buffer was removed. The cells were fixed by first antibody for 10 minutes and washed by a sterilized PBS buffer for three times and the sterilized PBS buffer was then removed. Next, secondary antibodies were added into the culturing plate and the culturing plate was placed in a 4° C. refrigerator protecting from light for 30 minutes. Hoechst33342 was added in the culturing plate for staining the cells for 15 minutes (protected from light) and then wash by a sterilized PBS buffer for three times.

Figure 13:
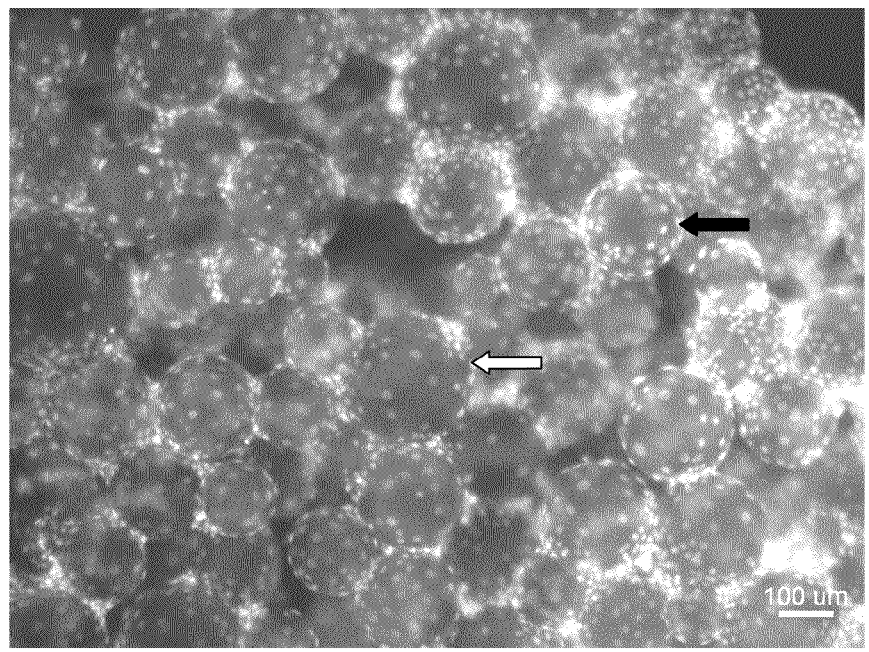
FIG. 13 shows the result for mixing and culturing different types of cells.

In FIG. 13, the position pointed out by the black arrow is cardiomyocytes, the position pointed out by the white arrow is mesenchymal stem cells and the white spots are cell nucleus stained by Hoechst33342. As shown in FIG. 13, the cells were able to attach on the gelatin microspheres and among the different types of cells. Specifically, the gelatin microspheres attached to the different types of cells, respectively, compactly connecting to each other.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for culturing cells by stacking cells in layers, comprising:
   (a) providing a first hydrophobic cell culture container, a second hydrophobic cell culture container and a third hydrophobic cell culture container, wherein the first hydrophobic cell culture container, the second hydrophobic cell culture container and the third hydrophobic cell culture container comprise a bottom made of a hydrophobic material or a bottom made of a non-hydrophobic material coated with a hydrophobic material, respectively;
   (b) adding first carriers which are more hydrophilic than the first hydrophobic cell culture container and a first type of cells into the first hydrophobic cell culture container, adding second carriers which are more hydrophilic than the second hydrophobic cell culture container and a second type of cells into the second hydrophobic cell culture container, adding third carriers which are more hydrophilic than the third hydrophobic cell culture container and a third type of cells into the third hydrophobic cell culture container;
   (c) culturing the first type of cells, the second type of cells and the third type of cells, respectively, wherein the first type of cells attach to the first carriers and grow, the second type of cells attach to the second carriers and grow, and the third type of cells attach to the third carriers and grow;
   (d) providing another hydrophobic cell culture container, wherein the other hydrophobic cell culture container comprises a bottom made of the hydrophobic material or a bottom made of the non-hydrophobic material coated with the hydrophobic material;
   (e) adding the first type of cells attached on the first carriers into the other hydrophobic cell culture container to form a first layer of cells on the bottom of the other hydrophobic cell culture container, then adding the second type of cells attached on the second carriers into the other hydrophobic cell culture container to form a second layer of cells on the first layer of cells, and then adding the third type of cells attached on the third carriers into the other hydrophobic cell culture container to form a third layer of cells on the second layer of cells; and
   (f) culturing the first layer of cells, the second layer of cells and the third layer of cells to make the first type of cells, the second type of cells and the third type of cells connect to each other to form cells stacked layer by layer.

2. The method for culturing cells by stacking cells in layers as claimed in claim 1, wherein the hydrophobic material comprises polydimethylsiloxane, polyethylene, polypropylene, polyvinylchloride, Teflon, polyethylene terephthalate or polycaprolactone.

3. The method for culturing cells by stacking cells in layers as claimed in claim 1, wherein the first carriers, the second carriers and the third carriers are biodegradable material.

4. The method for culturing cells by stacking cells in layers as claimed in claim 3, wherein the first type of cells is fibroblasts, the second type of cells is epidermal cells and the third type of cells is keratinocytes, and after the step (f), the first type of the cells, the second type of cells and the third type of cells become a skin tissue structure.

5. The method for culturing cells by stacking cells in layers as claimed in claim 3, wherein the first type of cells is limbal stem cells, the second type of cells is fibroblasts and the third type of cells is epithelial cells, and after the step (f), the first type of the cells, the second type of cells and the third type of cells become a limbal tissue structure.

6. The method for culturing cells by stacking cells in layers as claimed in claim 3, wherein the first type of cells is cardiomyocytes, the second type of cells is stem cells and the third type of cells is endothelial cells, and after the step (f), the first type of the cells, the second type of cells and the third type of cells become a cardiac tissue structure.

7. A method for mixing and culturing cells, comprising:
   (a) providing a first hydrophobic cell culture container and a second hydrophobic cell culture container, wherein the first hydrophobic cell culture container and the second hydrophobic cell culture container comprise a bottom made of a hydrophobic material or a bottom made of a non-hydrophobic material coated with a hydrophobic material, respectively;
   (b) adding first carriers which are more hydrophilic than the first hydrophobic cell culture container and a first type of cells into the first hydrophobic cell culture container, and adding second carriers which are more hydrophilic than the second hydrophobic cell culture container and a second type of cells into the second hydrophobic cell culture container;
   (c) culturing the first type of cells and the second type of cells, respectively, wherein the first type of cells attach to the first carriers and grow, and the second type of cells attach to the second carriers and grow;
   (d) providing another hydrophobic cell culture container, wherein the other hydrophobic cell culture container comprises a bottom made of the hydrophobic material or a bottom made of the non-hydrophobic material coated with the hydrophobic material;
   (e) mixing the first type of cells attached on the first carriers and the second type of cells attached on the second carriers to form a mixture of first type of cells attached on the first carriers and the second type of cells attached on the second carriers and adding the mixture into the other hydrophobic cell culture container; and (f) culturing the mixture.

8. The method for mixing and culturing cells as claimed in claim 7, wherein the hydrophobic material comprises polydimethylsiloxane, polyethylene, polypropylene, polyvinylchloride, Teflon, polyethylene terephthalate or polycaprolactone.

9. The method for mixing and culturing cells as claimed in claim 7, wherein the first type of cells attached on the first carriers and the second type of cells attached on the second carriers are mixed by a ratio.

10. The method for mixing and culturing cells as claimed in claim 7, wherein the first type of cells is stem cells and the second type of cells is nerve cells.

11. The method for mixing and culturing cells as claimed in claim 7, wherein the first type of cells is stem cells and the second type of cells is chondrocytes.

12. The method for mixing and culturing cells as claimed in claim 7, wherein the first type of cells is hair follicle stem cells and the second type of cells is epithelial cells.

13. The method for mixing and culturing cells as claimed in claim 10, wherein a mixing ratio for the stem cells to the nerve cells is about 100:1-1:100.

* * * * *